(12) United States Patent
Barrows

(10) Patent No.: US 11,119,339 B1
(45) Date of Patent: Sep. 14, 2021

(54) PROTECTIVE LOUPES EYEWEAR ASSEMBLY

(71) Applicant: Andrew Barrows, Maple Grove, MN (US)

(72) Inventor: Andrew Barrows, Maple Grove, MN (US)

( * ) Notice: Subject to any disclaimer, the term of this patent is extended or adjusted under 35 U.S.C. 154(b) by 246 days.

(21) Appl. No.: 16/437,602

(22) Filed: Jun. 11, 2019

Related U.S. Application Data

(60) Provisional application No. 62/683,324, filed on Jun. 11, 2018.

(51) Int. Cl.
*G02C 9/04* (2006.01)
*G02C 7/08* (2006.01)
*G02C 7/10* (2006.01)

(52) U.S. Cl.
CPC ............... *G02C 9/04* (2013.01); *G02C 7/088* (2013.01); *G02C 7/104* (2013.01)

(58) Field of Classification Search
CPC ........... G02C 9/04; G02C 7/104; G02C 7/088
See application file for complete search history.

(56) References Cited

U.S. PATENT DOCUMENTS

| 6,371,612 B1* | 4/2002 | Barrows | A61F 9/022 351/128 |
| 2013/0278893 A1* | 10/2013 | Lemay | G02C 7/104 351/159.57 |

\* cited by examiner

*Primary Examiner* — Tuyen Tra
(74) *Attorney, Agent, or Firm* — Eggink & Eggink; Anthony G. Eggink; Katrina M. Eggink

(57) ABSTRACT

A protective loupes eyewear assembly having an eyewear frame with magnifying loupes. The eyewear frame has notches in the top of the frame and a bottom shelf structure on the inside of the frame. An insert assembly with a pair of outwardly extending tabs and a mating configuration is constructed to slip into the notches at the top of the eyewear frame and into a bottom shelf structure behind the eyewear frame to provide laser protection for use in the dental, surgical and other arts.

19 Claims, 4 Drawing Sheets

PROTECTIVE LOUPES EYEWEAR ASSEMBLY

This Application claims the benefit of U.S. Provisional Application Ser. No. 62/683,324, filed Jun. 11, 2018, entitled Protective Loupes Eyewear Assembly, and is fully incorporated by reference herein.

BACKGROUND OF THE INVENTION

The present invention relates generally to eyewear and particularly to protective loupes eyewear. More particularly, the invention relates to loupes eyewear with a laser protective insert assembly.

The use of laser equipment is common in the dental and medical arts. To protect the eyes of the laser device user, protective eyewear is recommended and required. Typically, the dentist or physician utilizes eyewear with magnifying loupes when working with the laser equipment. These eyewear structures restrict the ability to provide protective eyewear for the user because the loupes are positioned in front of the eyeglass lenses thereby necessitating the positioning of the protective laser filter lenses against the back or the inside of the eyeglasses.

Although prior art eyewear assemblies have been proposed and utilized to protect the eyes of dentists, physicians and other laser device users wearing loupes eyewear, the laser protective structure typically requires assembly before the loupes eyewear is utilized. Because the laser protection is not always required when the loupes eyewear is worn by the dentist or surgeon, a need exists in the dental and medical arts to provide a protective loupes eyewear assembly that is easily assembled and utilized when necessary, i.e., during the course of a dental or medical procedure.

The protective loupes eyewear assembly of the present invention provides an improvement and overcomes the difficulties and limitations of the prior art by providing a protective slip-in insert structure which matingly engages the inside of the eyeglass frame and which is easily positioned on the inside of loupes eyewear.

SUMMARY OF THE INVENTION

A protective loupes eyewear assembly having an eyewear frame with magnifying loupes extending outwardly therefrom. The top of the eyewear frame has notches therein and a bottom shelf structure on the inside of the frame.

An insert assembly having a mating configuration with the eyewear frame and which is constructed to be positioned and slipped inside and behind the lenses of the eyewear frame. A pair of outwardly extending tab members are provided on the top of the insert assembly for positioning the tab members into the notches at the top of the eyewear frame. The bottom edge of the insert has a configuration for positioning and resting in the inside bottom shelf structure of the eyewear frame.

The insert assembly has a lens structure which absorbs laser light of a specified wavelength or wavelength range.

An advantage of the protective loupes eyewear assembly of the invention is to provide an easy to utilize protective structure wherein the protective laser insert entirely slips in and is secured behind the loupes eyewear frame.

Another advantage is to provide a protective laser insert which mates into the inside of loupes eyewear and which may be easily slipped in and removed during the course of a dental or medical procedure.

These and other advantages of this invention will become clear from the following description by reference to the drawings.

DESCRIPTION OF THE PREFERRED EMBODIMENTS

Figure 1:
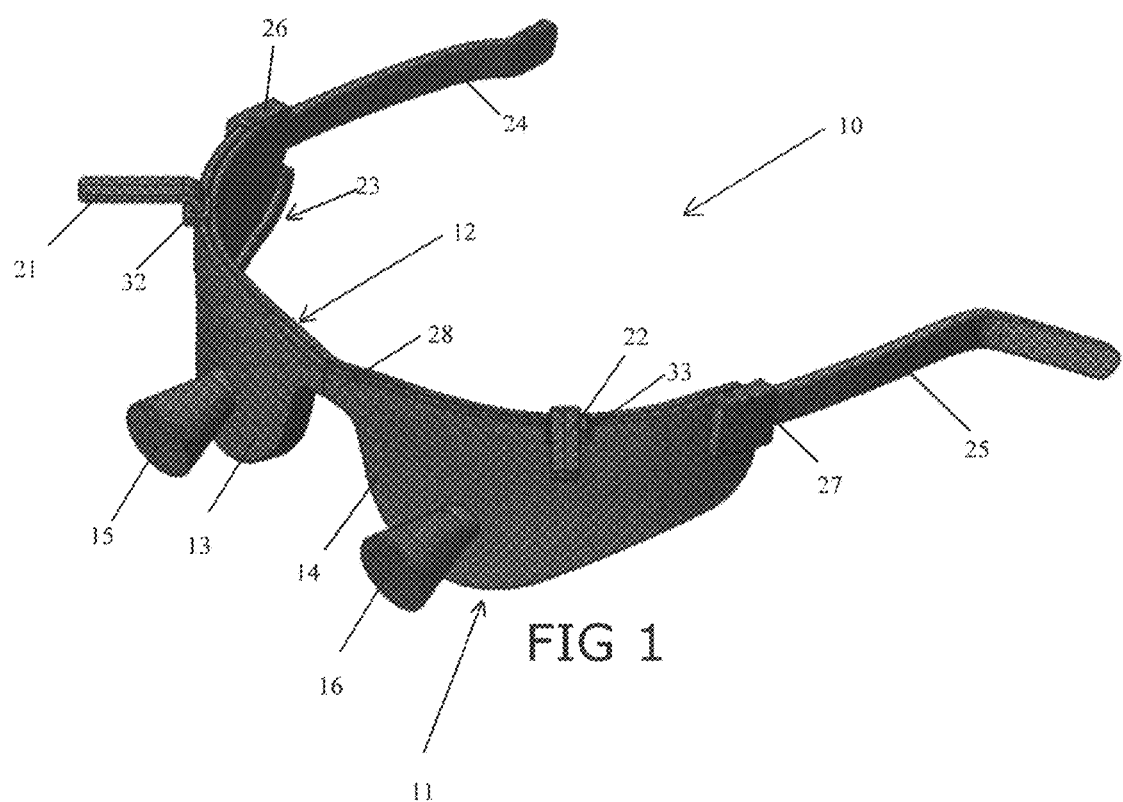
FIG. 1 is a perspective view showing the protective loupes eyewear assembly of the invention.
Figure 2:
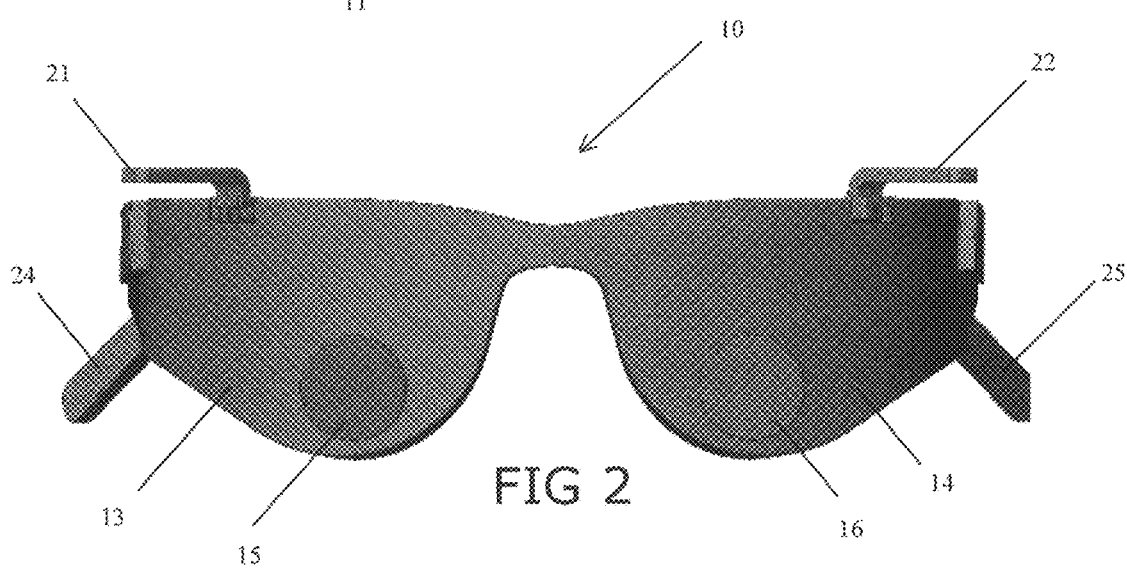
FIG. 2 is a frontal perspective view showing the invention of FIG. 1.
Figure 3:
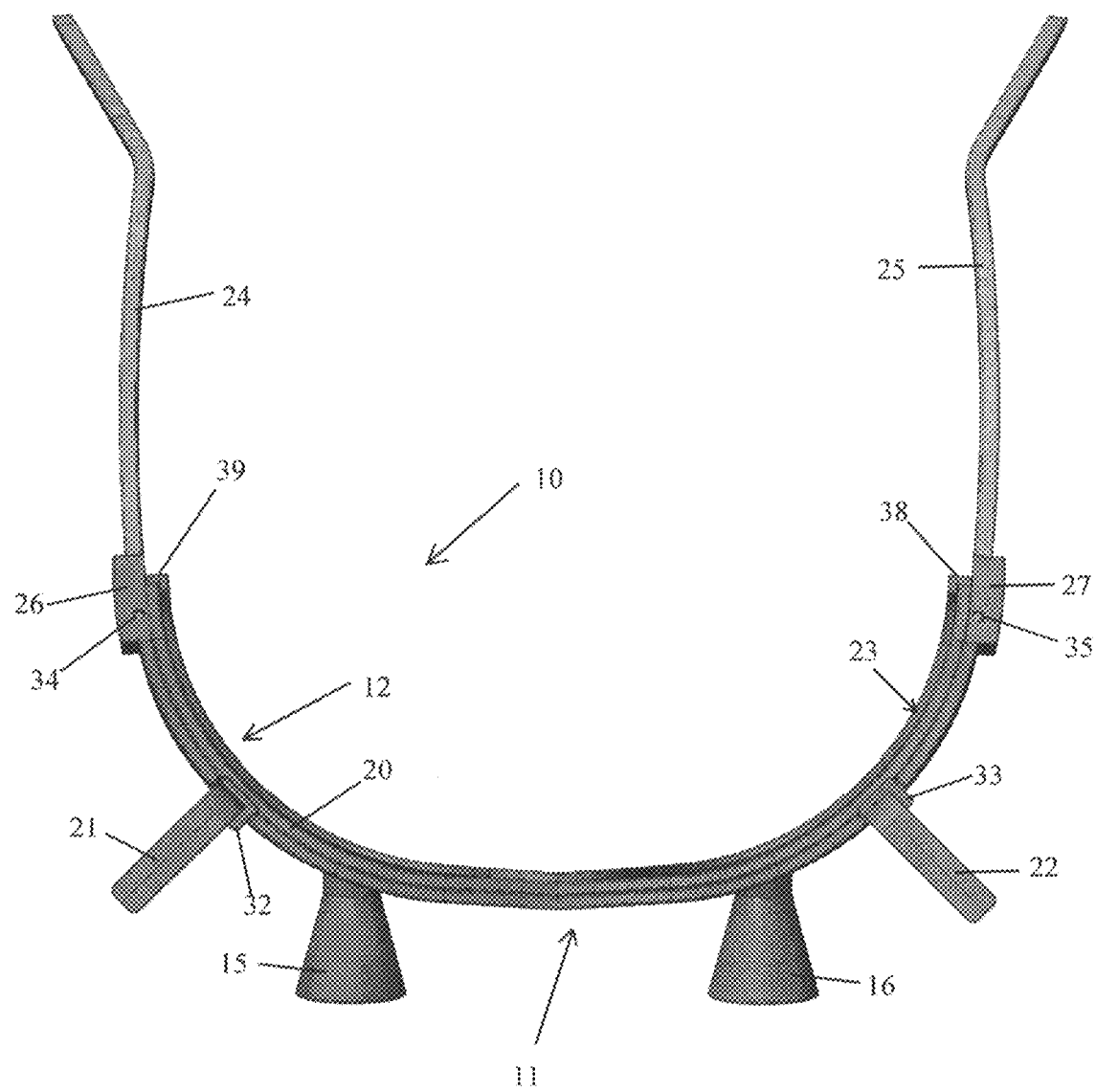
FIG. 3 is a top perspective view of the protective loupes eyewear assembly of FIG. 1.

Referring to FIGS. 1-3, the protective loupes eyewear assembly 10 is shown comprised of an eyewear frame 11 and a mating insert assembly 12 positioned on the inside of the eyewear frame 11. The cooperating eyewear frame 11 and insert assembly 12 are shown to have generally the same frontal shape and configuration. The eyewear frame 11 is a curved structure to protect the eyes of the wearer, i.e. a dentist or physician engaged in a dental or surgical procedure utilizing laser equipment. The eyewear frame 11 is shown having a nose bridge portion 28 and holding curved lenses 13 and 14 between the upper, lower and side portions of the eyewear frame 11. Loupes 15 and 16 are shown extending outwardly from lenses 13 and 14, respectively. Loupes 15 and 16 are known in the dental and medical arts and are mounted to eyeglasses to provide in lens magnification thereby allowing the wearer to see small details more closely.

As further shown, eyewear frame 11 has hinges 26 and 27 and temples 24 and 25 extending therefrom for engaging the lateral portions and top of the ears of the wearer. The temples 24, 25 are shown joined to hinges 26, 27, respectively, by means of pin/screws 34, 35 as is known in the eyewear art. Although a curved, wrap around style eyewear frame is shown in FIGS. 1-3, other eyewear styles may be utilized in accordance with the teachings of the present invention. The curved lenses 13, 14 provide the wearer with increased side eye protection. The insert assembly 12 is shown to have a shape and configuration to matingly slip behind the eyewear frame 11.

Figure 4:
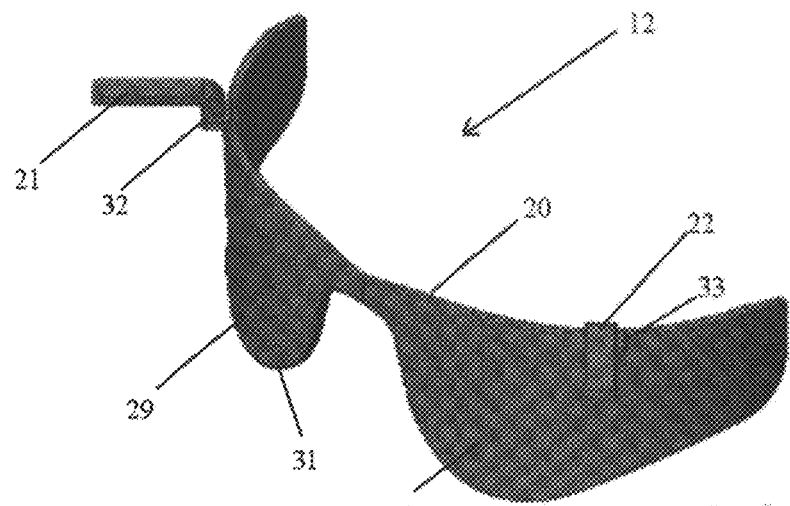
FIG. 4 is a perspective view showing the insert assembly of the invention.
Figure 5:
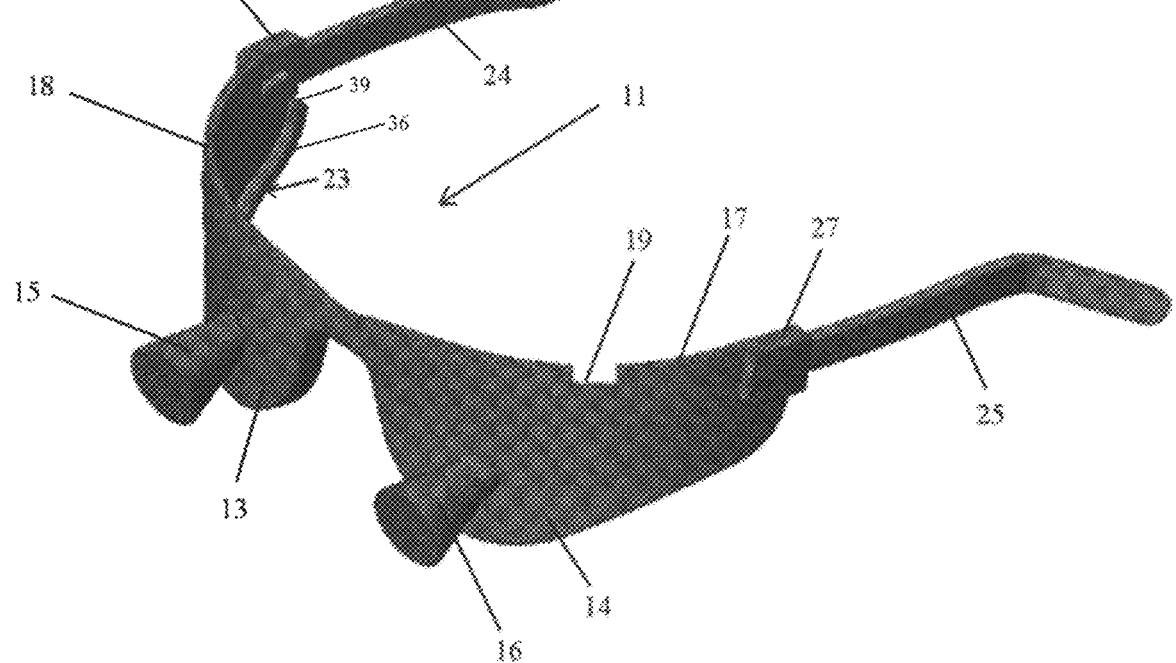
FIG. 5 is a perspective view showing the eyewear frame with loupes.

Referring further to FIGS. 4 and 5, the insert assembly 12 shown in FIG. 4 and the eyewear frame 11 shown in FIG. 5 are shown in their separated state. Eyewear frame 11 is shown to have notches, or slots, 18 and 19 at the frame top 17 which are shown to be generally rectangular in shape. The interior bottom of frame 11 is shown to have a shelf like structure 23 which is further shown in FIGS. 6 and 7. FIG. 4 shows the insert assembly 12 being a unitary structure having outwardly extending tab structure 21 and 22. The tab structures 21 and 22 have base members 32 and 33, respectively, and which are positioned for placement in notches 18 and 19, respectively. The base members 32, 33 are shown to have generally rectangular configurations. The perpendicularly, outwardly extending tabs 21 and 22 are elongated and adapted to not impede vision and to be easily grasped by the wearer. The bottom edge 31 of the insert assembly 12 is configured to be slipped into and secured in the interior bottom ledge or channel 23 of the eyewear frame 11. The tabs 21 and 22 provide the wearer with the means to easily manipulate the insert assembly 12 into and from the eyewear frame 11, as may be required during the course of a dental or medical procedure, for example.

Figure 6:
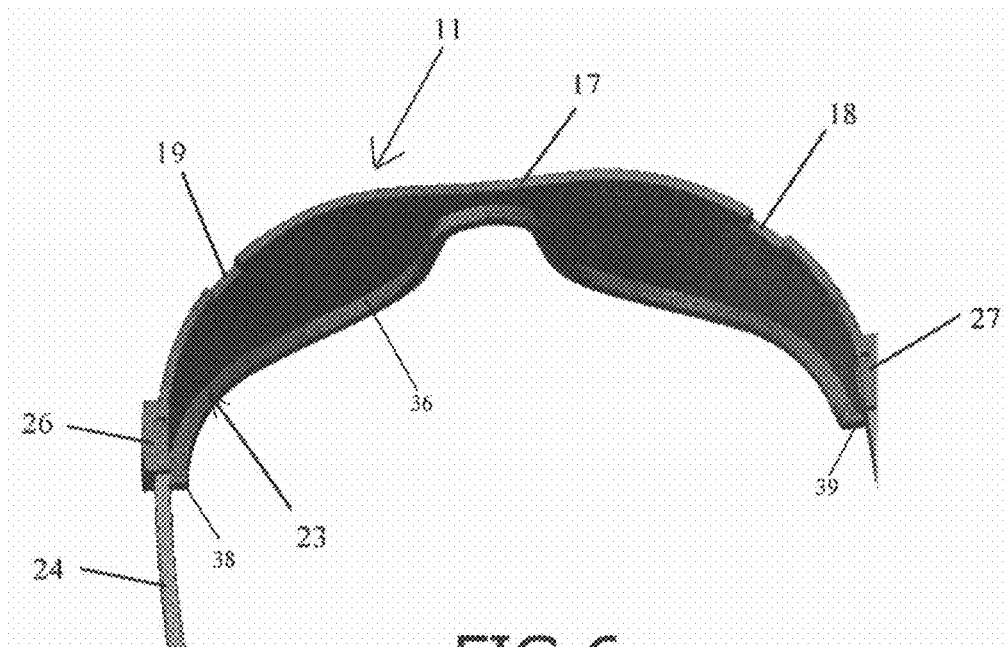
FIG. 6 is a perspective view showing the inside of the eyewear frame of FIG. 5.

The base structures 32 and 33 and tabs 21 and 22, as particularly shown in FIG. 4, extend generally perpendicularly from the top 20 of the insert assembly 12. As shown further in FIGS. 6 and 7, the interior bottom ledge 23 of the eyewear frame 11 has a peripheral lip 36 defining shoulder 37 which capture the bottom edge 31 of the insert assembly 12. The curvilinear configuration of the bottom edge 31, i.e., defining the bottom of lens portions 29 and 30, is captured in the curvilinear configuration of the bottom ledge 23 of the eyewear frame 11. The shoulder 37 has a width adapted to receive the bottom edge 31 thickness of the insert assembly 12. End lip portions 38 and 39 of the interior bottom ledge 23 are shown in FIG. 6, and as shown in FIG. 7, the bottom edge 31 of the insert assembly 12 is captured and positioned between frame top 17 and lip 36 at the nose bridge 28 of the eyewear frame 11.

Figure 7:
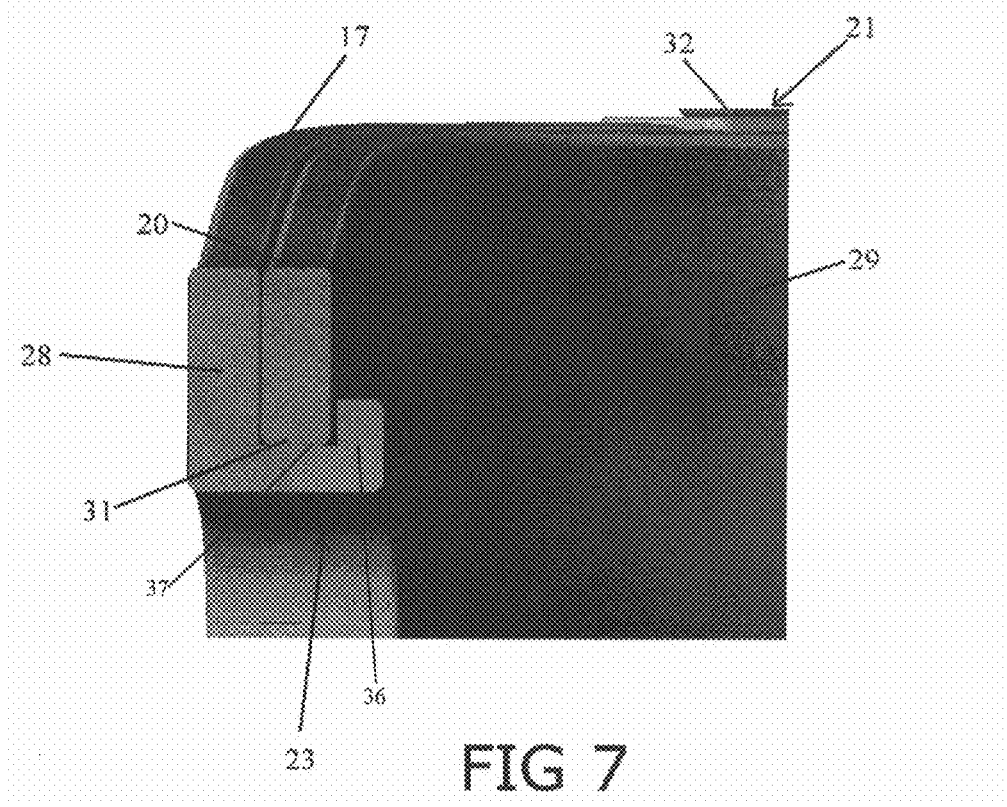
FIG. 7 is an enlarged sectional view taken at the nose bridge showing the insert assembly positioned within the continuous inside bottom ledge of the eyewear frame.

FIG. 7 is an enlarged sectional view taken at the nose bridge 28 of the eyewear frame 11 and showing the top 20 and bottom edge 31 of insert assembly 11 slipped in and positioned within the interior bottom ledge of eyewear frame 11. The insert assembly 12 is shown matingly aligned with the eyewear frame 11.

When in position, the lenses 29 and 30 of the insert assembly 12 provide laser protection for the lenses 13 and 14 of the eyewear frame 11. The lenses 29 and 30 are constructed of laser filter lenses for use with various laser light wavelength sources. For example, insert lenses may be provided for dental related lasers emanating laser wavelengths of 800-830 nm OD5, 735-1064 nm OD 5 and 1064 nm OD 7. Lenses may be provided to filter any laser light wavelength utilized in the various arts.

The eyewear frame 11 and insert assembly 12 may be constructed of polymeric materials or other materials utilized in the eyewear arts. The lenses 29 and 30 of the insert assembly 12 may be formed of a polycarbonate material, glass or other material adapted to absorb laser light.

The protective loupes eyewear assembly 10 provides an eyewear frame 11 having a removable insert assembly 12 with a mating shape and configuration which permits a wearer to easily remove and reposition the laser light protective insert assembly 12 behind the eyewear frame 11 by means of the cooperating tab structures 21, 22 and notches 18, 19 and cooperating bottom edge 31 and interior bottom ledge 23 of the insert assembly 12 and eyewear frame 11, respectively.

As many changes are possible to the protective loupes eyewear assembly embodiments of this invention utilizing the teachings thereof, the descriptions above, and the accompanying drawings should be interpreted in the illustrative and not in the limited sense.

That which is claimed is:

1. A protective loupes eyewear assembly comprising:
   a) an eyewear frame having an exterior, an interior, a top portion, a bottom portion and having a pair of lenses with loupes extending outwardly therefrom, said top portion of said eyewear frame having spaced notches therein and said bottom portion of said eyewear frame having a ledge extending along its interior;
   b) a removable insert assembly constructed of a laser light absorbing material and adapted to cover said pair of lenses in said interior of said eyewear frame, said insert assembly having a top portion with spaced tab members for engaging and positioning within said spaced notches of said eyewear frame, said insert assembly having a bottom edge adapted to slip into and rest within said ledge of said bottom portion of said eyewear frame.

2. The protective loupes eyewear assembly of claim 1, wherein said tab members of said removable insert assembly further having a base portion for engaging said spaced notches in said eyewear frame and wherein said tab members extend generally perpendicularly outward said eyewear assembly when said insert assembly is positioned behind said eyewear frame.

3. The protective loupes eyewear assembly of claim 1, wherein said ledge of said bottom portion of said eyewear frame comprises a peripheral shoulder portion and a peripheral lip portion to capture said bottom edge of said removable insert assembly.

4. The protective loupes eyewear assembly of claim 1, wherein said top and bottom of said eyewear frame are curvilinear and continuous in shape.

5. The protective loupes eyewear assembly of claim 1, wherein said insert assembly absorbs laser light waves of 800-830 nm OD 5, 735-2064 nm OD 5 and 1064 nm OD 7.

6. The protective loupes eyewear assembly of claim 1, wherein said eyewear frame and insert assembly are constructed of polymeric materials and wherein said eyewear frame has a brow bar and a pair of temples.

7. A protective loupes eyewear assembly comprising:
   a) an eyewear frame having an exterior, interior, and a pair of lenses having loupes extending outwardly therefrom, said eyewear frame having a top and bottom with respect to said lenses, said top having a notch above each said lens and a bottom shelf structure below said lenses and facing said interior,
   b) an insert assembly having a configuration for covering said interior of said eyewear frame, said insert assembly having outwardly extending tab members for engaging and positioning within said notches of said eyewear frame, said insert assembly further having a bottom edge configuration for resting and slip in positioning into said shelf structure of said eyewear frame, and
   c) said insert assembly constructed of a laser absorbing material.

8. The protective loupes eyewear assembly of claim 7, wherein said top and bottom of said eyewear frame are curvilinear and continuous in shape.

9. The protective loupes eyewear assembly of claim 8, wherein said bottom shelf structure of said eyewear frame is continuous and of a curvilinear shape and adapted for receiving said bottom edge of said insert.

10. The protective loupes eyewear assembly of claim 7, wherein said insert assembly absorbs laser light of a specified wavelength range.

11. The protective loupes eyewear assembly of claim 10, wherein said insert assembly absorbs laser light waves of 800-830 nm OD 5, 735-2064 nm OD 5 and 1064 nm OD 7.

12. The protective loupes eyewear assembly of claim 7, wherein said eyewear frame and insert assembly are constructed of polymeric materials.

13. The protective loupes eyewear assembly of claim 7, wherein said eyewear frame has a brow bar and a pair of temples.

14. The protective loupes eyewear assembly of claim 7, wherein said outwardly extending tab members have a base, said base being constructed and arranged to engage said notches of said eyewear frame.

15. A protective loupes eyewear assembly comprising:
a) an eyewear frame having a top, a bottom, an exterior and an interior and having a pair of lenses with loupes extending outwardly therefrom, said eyewear frame having a predetermined shape and configuration; and
b) an insert assembly having a top and bottom portion and constructed of a laser light absorbing material and having generally the same shape and configuration as said eyewear frame, said eyewear frame and said insert assembly having cooperating top and bottom securement structures to permit the easy removal and positioning of said insert assembly behind said eyewear frame, wherein said top and bottom securement structures of said loupes eyewear assembly comprise a pair of notches in said top of said eyewear frame and a ledge extending along said bottom and interior of said eyewear frame and wherein said cooperating top and bottom securement structures of said insert assembly comprise spaced tab members extending outwardly from said top portion and a bottom edge for engaging said pair of notches and said ledge of said eyewear frame, respectively.

16. The protective loupes eyewear assembly of claim 15, wherein said eyewear frame and insert assembly are constructed of polymeric materials and wherein said eyewear frame has a brow bar and a pair of temples.

17. The protective loupes eyewear assembly of claim 15, wherein said spaced tab members further having a base portion, said base portion being constructed and arranged to engage said notches of said eyewear frame.

18. The protective loupes eyewear assembly of claim 15, wherein said insert assembly absorbs laser light waves of 800-830 nm OD 5, 735-2064 nm OD 5 and 1064 nm OD 7.

19. The protective loupes eyewear assembly of claim 15, wherein said top and bottom of said eyewear frame are curvilinear and continuous in shape.

\* \* \* \* \*